US011969151B2

(12) United States Patent
Suzuki et al.

(10) Patent No.: US 11,969,151 B2
(45) Date of Patent: Apr. 30, 2024

(54) ENDOSCOPE

(71) Applicant: OLYMPUS CORPORATION, Tokyo (JP)

(72) Inventors: Takuji Suzuki, Hachioji (JP); Kazuki Honda, Higashiyamato (JP); Mikio Inomata, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 568 days.

(21) Appl. No.: 17/113,402

(22) Filed: Dec. 7, 2020

(65) Prior Publication Data

US 2021/0085157 A1 Mar. 25, 2021

Related U.S. Application Data

(63) Continuation of application No. PCT/JP2019/008373, filed on Mar. 4, 2019.

(30) Foreign Application Priority Data

Jun. 8, 2018 (JP) .................................. 2018-110117

(51) Int. Cl.
*A61B 1/00* (2006.01)
(52) U.S. Cl.
CPC ...... *A61B 1/00163* (2013.01); *A61B 1/00096* (2013.01)
(58) Field of Classification Search
CPC ............. A61B 1/0008; A61B 1/00096; A61B 1/00163; A61B 1/00188; A61B 1/05; A61B 1/051; A61B 1/07
See application file for complete search history.

(56) References Cited

U.S. PATENT DOCUMENTS

2009/0173875 A1* 7/2009 Ichimura ............ A61B 1/00096
250/216
2014/0176692 A1* 6/2014 Tsuyuki ................. H04N 23/56
348/71
(Continued)

FOREIGN PATENT DOCUMENTS

EP 2875772 A1 5/2015
JP H08-224207 A 9/1996
(Continued)

OTHER PUBLICATIONS

International Search Report dated Jun. 4, 2019 issued in PCT/JP2019/008373.

*Primary Examiner* — Aaron B Fairchild
(74) *Attorney, Agent, or Firm* — Scully, Scott, Murphy & Presser, P.C.

(57) ABSTRACT

An endoscope includes: a distal end rigid member including a distal end-side end portion and a proximal end-side end portion in the longitudinal axis direction of an insertion portion and a hole provided in the longitudinal axis direction; an objective optical unit inserted into and attached to an inside of the hole in the longitudinal axis direction; a camera unit; and a projecting portion projecting from at least a part of a periphery of the hole, from the proximal end-side end portion to a proximal end side in the longitudinal axis direction, by a length that is equal to or greater than a length up to a gravity center position of the camera unit in the longitudinal axis direction exceeding a connecting portion connecting the objective optical unit and the camera unit, so as to cover a part of an outer peripheral portion of the camera unit.

20 Claims, 12 Drawing Sheets

(56) References Cited

U.S. PATENT DOCUMENTS

| | | | | |
|---|---|---|---|---|
| 2014/0288370 A1* | 9/2014 | Jungbauer | .......... | A61B 1/00105 |
| | | | | 600/112 |
| 2014/0330081 A1* | 11/2014 | Imai | .................... | A61B 1/0008 |
| | | | | 600/129 |
| 2016/0213225 A1* | 7/2016 | Sato | ........................ | A61B 1/005 |
| 2018/0092515 A1* | 4/2018 | Yashiro | .............. | A61B 1/00181 |

FOREIGN PATENT DOCUMENTS

| | | |
|---|---|---|
| JP | H10-151106 A | 6/1998 |
| JP | 5315482 B1 | 10/2013 |
| WO | WO 2014/013787 A1 | 1/2014 |
| WO | WO 2017/183371 A1 | 10/2017 |

\* cited by examiner

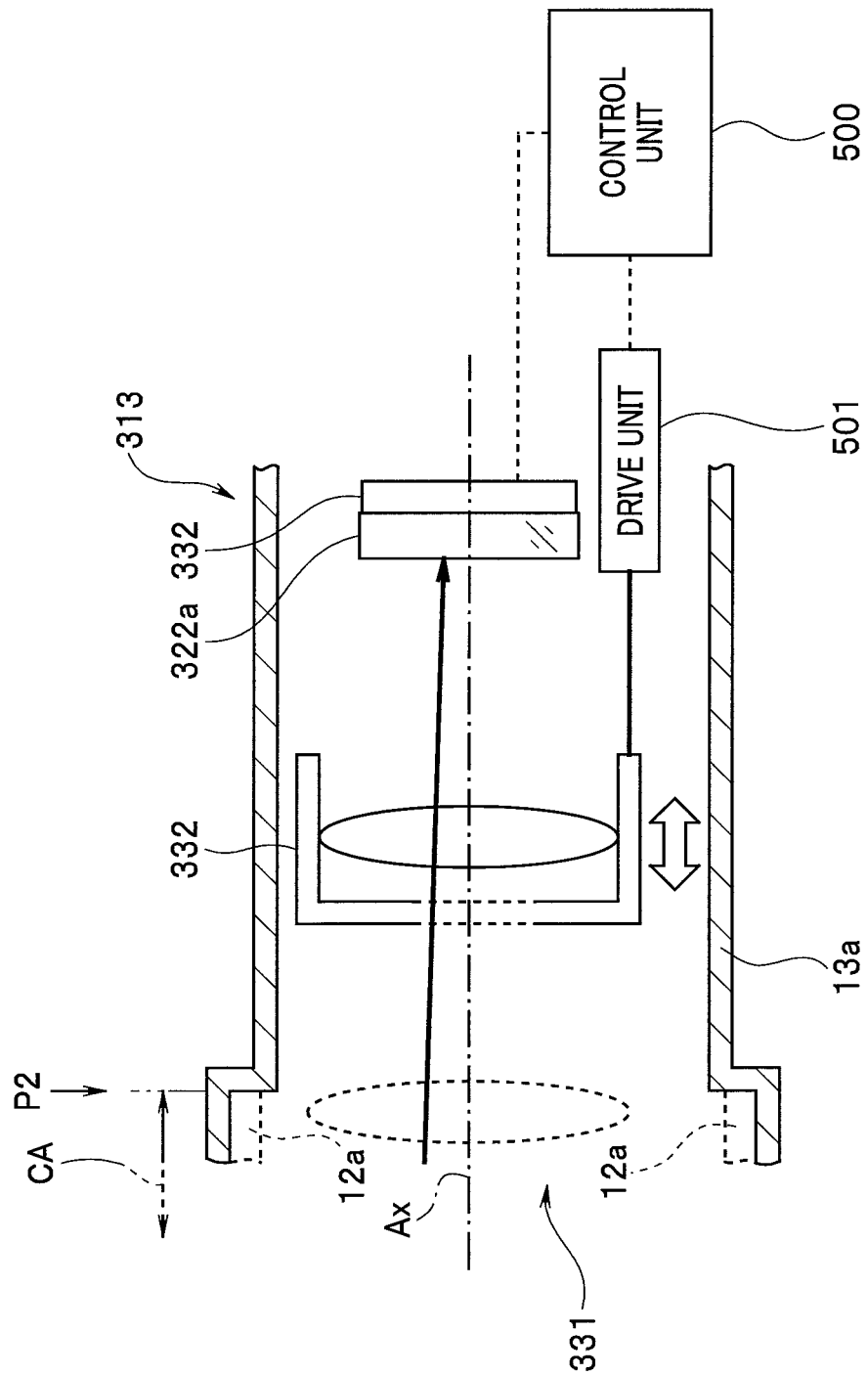

ENDOSCOPE

CROSS REFERENCE TO RELATED APPLICATION

This application is a continuation application of PCT/JP2019/008373 filed on Mar. 4, 2019, and claims benefit of Japanese Application No. 2018-110117 filed in Japan on Jun. 8, 2018, the entire contents of which are incorporated herein by this reference.

BACKGROUND OF THE INVENTION

1. Field of the Invention

The present invention relates to an endoscope, and particularly to an endoscope including two optical systems inside a distal end portion of an insertion portion.

2. Description of the Related Art

In the related art, endoscopes have widely been used in the medical field and the industrial field. An endoscope has an insertion portion and an operation portion. An image pickup unit is provided at a distal end portion of the elongated insertion portion and acquires an image of a subject. A person who performs endoscope inspection can cause a display device to display an image inside the subject and inspect inside the subject by inserting the insertion portion into the subject.

The image pickup unit provided at the distal end portion of the insertion portion includes an objective optical unit and a camera unit. The objective optical unit includes a plurality of optical members such as lenses, and the camera unit includes an image pickup device. Light from the subject that has passed through the objective optical unit forms an image on an image pickup surface of the image pickup device, and the image pickup device performs photoelectric conversion on a subject image and outputs an image pickup signal.

The insertion portion includes, from the distal end, a distal end portion, a bending portion, and a flexible tube portion, and a person who performs endoscope inspection can view an endoscope image at a site in the subject in a desired direction by operating a bending operation member provided at the operation portion.

Typically, the image pickup device is disposed at the distal end portion of the insertion portion such that the image pickup surface of the image pickup device of the camera unit perpendicularly intersects an optical axis of the objective optical unit, as disclosed in Japanese Patent Application Laid-Open Publication No. 8-224207. In the endoscope disclosed in Japanese Patent Application Laid-Open Publication No. 8-224207, the objective optical unit is fitted to a frame member of the camera unit.

SUMMARY OF THE INVENTION

An endoscope according to an aspect of the present invention includes: a distal end rigid member disposed on a distal end side of an insertion portion of the endoscope in a longitudinal axis direction and including a distal end-side end portion and a proximal end-side end portion in the longitudinal axis direction and a hole provided in the longitudinal axis direction; a first optical system inserted into and attached to an inside of the hole in the distal end rigid member in the longitudinal axis direction; a second optical system connected to a proximal end side of the first optical system in the longitudinal axis direction and provided on a proximal end side in the longitudinal axis direction relative to the proximal end-side end portion of the distal end rigid member; and a projecting portion projecting from at least a part of a periphery of the hole in the distal end rigid member, the projecting portion projecting from the proximal end-side end portion of the distal end rigid member to a proximal end side in the longitudinal axis direction by a length that is equal to or greater than a length up to a gravity center position of the second optical system in the longitudinal axis direction exceeding a connecting portion connecting the first optical system and the second optical system, so as to cover a part of an outer peripheral portion of the second optical system.

An endoscope according to an aspect of the present invention includes: a distal end rigid member disposed on a distal end side of an insertion portion of the endoscope in a longitudinal axis direction and including a distal end-side end portion and a proximal end-side end portion in the longitudinal axis direction and a hole provided in the longitudinal axis direction; a first optical system inserted into and attached to an inside of the hole in the distal end rigid member in the longitudinal axis direction; a second optical system connected to a proximal end side of the first optical system in the longitudinal axis direction and provided on a proximal end side in the longitudinal axis direction relative to the proximal end-side end portion of the distal end rigid member; and a projecting portion projecting from at least a part of a periphery of the hole in the distal end rigid member, the projecting portion projecting from the proximal end-side end portion of the distal end rigid member to a proximal end side in the longitudinal axis direction by a length that is equal to or greater than a length to a proximal end portion of a connecting portion connecting the first optical system and the second optical system, the projecting portion covering a part of an outer peripheral portion of the second optical system with an inner peripheral portion of a portion provided to continue to the hole.

BRIEF DESCRIPTION OF THE DRAWINGS

FIG. 21 is a diagram illustrating a main configuration of a camera unit according to a ninth modification of the embodiment of the present invention.

DETAILED DESCRIPTION OF THE PREFERRED EMBODIMENT

Figure 1:
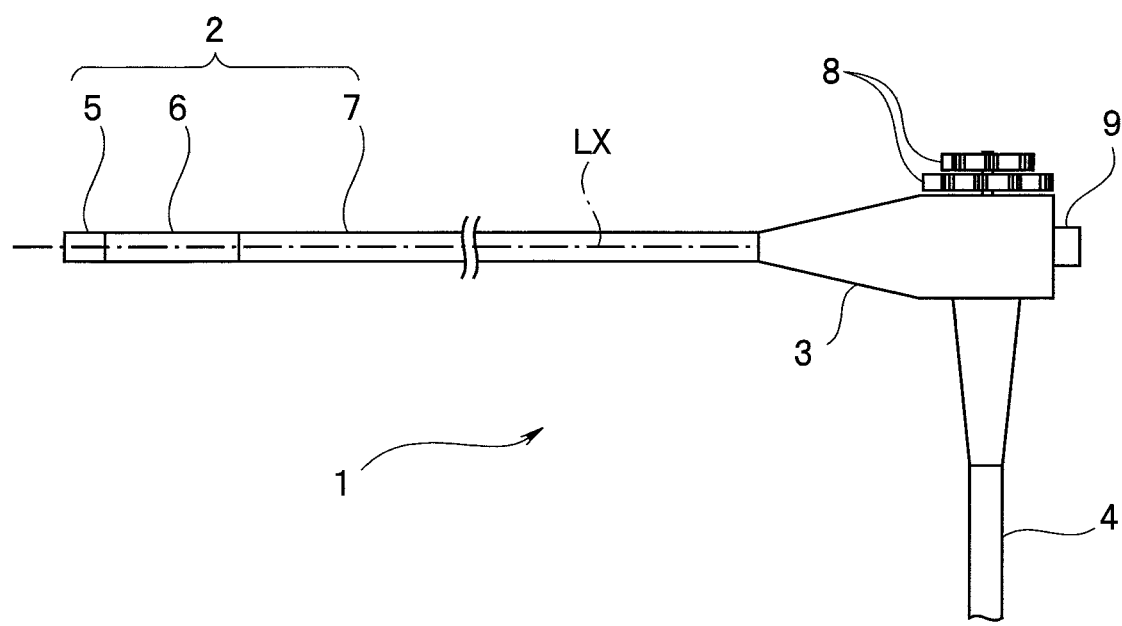
FIG. 1 is a configuration diagram of an endoscope according to an embodiment of the present invention.

Hereinafter, an embodiment of the present invention will be described with reference to drawings.

Note that different scales are used for components in each drawing used for the following description to illustrate each component with a size with which the component can be recognized in the drawing, and the present invention is not limited only to the numbers of components, the shapes of the components, the ratios of the sizes of the components, and the relative positional relationships of the respective components illustrated in these drawings.

Configuration

FIG. 1 is a configuration diagram of an endoscope according to the embodiment.

An endoscope 1 includes an insertion portion 2, an operation portion 3 to which a proximal end portion of the insertion portion 2 is connected, and a cable 4 extending from the operation portion 3.

The insertion portion 2 is elongated and can be inserted into a subject. The insertion portion 2 includes a distal end portion 5, a bending portion 6, and a flexible tube portion 7 from the distal end along a longitudinal axis LX. A plurality of internal components extending in a direction of the longitudinal axis LX are provided inside the insertion portion 2.

The operation portion 3 is provided with two disk-shaped turning knobs 8 for performing a bending operation of the bending portion 6 and a plurality of operation buttons 9 for a freeze operation and the like.

The bending portion 6 can be bent in the up, down, left, and right directions through turning operations of the two turning knobs 8.

A distal end portion of the cable 4 is provided with a connector, which is not illustrated, and a video processor or the like is connected to the distal end portion.

The endoscope 1 is used with a video processor, a light source device, a monitor, and the like. For example, a user such as an operator can perform inspection or the like while viewing an endoscope image of the subject displayed on a monitor using the endoscope 1.

Figure 2:
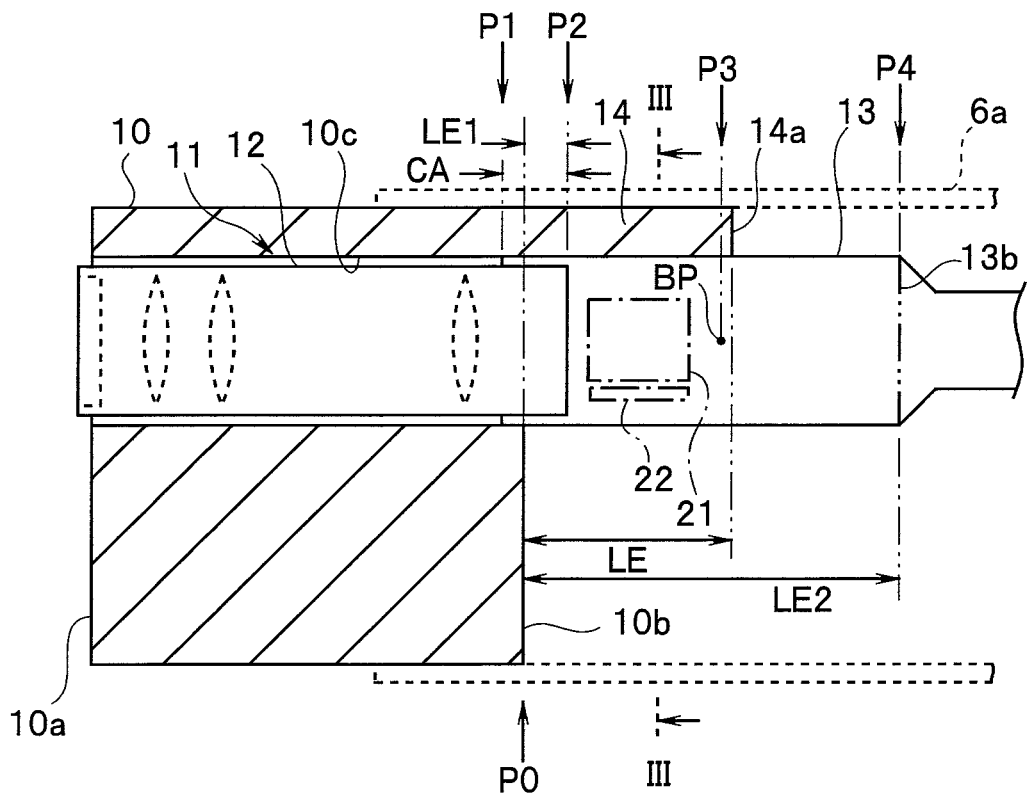
FIG. 2 is a schematic sectional view illustrating a configuration of a distal end portion of an insertion portion according to the embodiment of the present invention.
Figure 3:
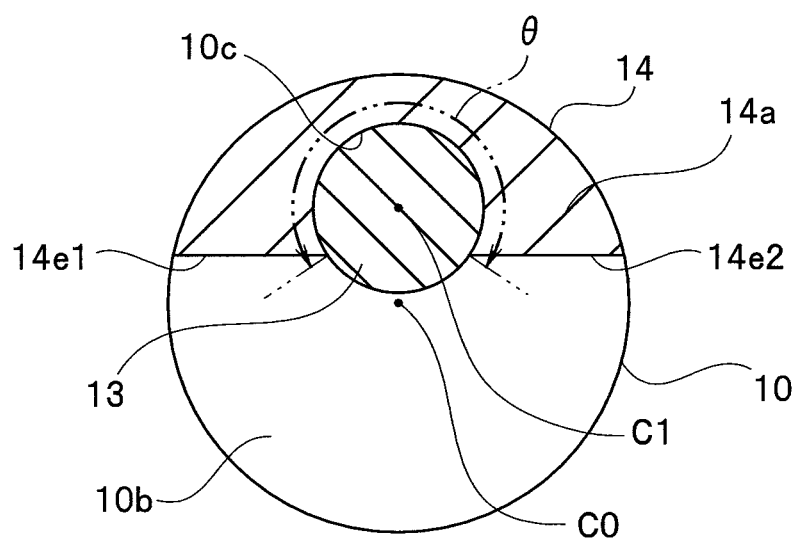
FIG. 3 is a sectional view of a distal end rigid member and an image pickup unit along a line III-III in FIG. 2.
Figure 4:
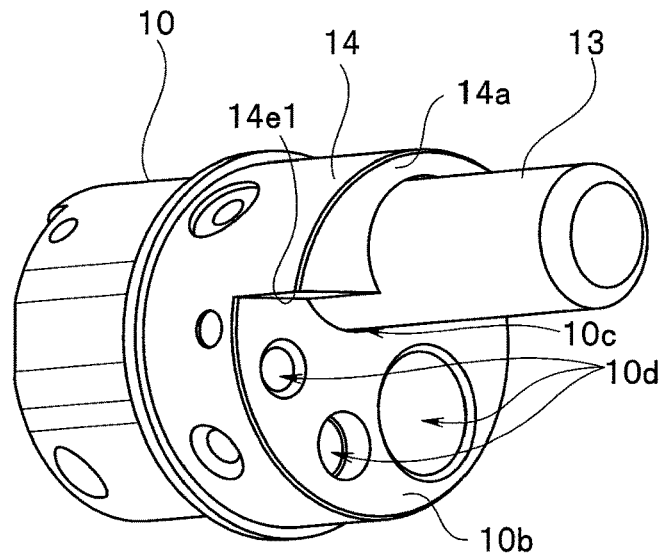
FIG. 4 is a perspective view of the distal end rigid member when seen from an obliquely back side, according to the embodiment of the present invention.

FIG. 2 is a schematic sectional view illustrating a configuration of the distal end portion 5 of the insertion portion 2. FIG. 2 illustrates only an image pickup unit secured to a distal end rigid member 10 of the distal end portion 5, and a distal end cap, an outer skin, other internal components, and the like of the distal end portion 5 are omitted. FIG. 3 is a sectional view of the distal end rigid member 10 and the image pickup unit along a line III-III in FIG. 2. FIG. 4 is a perspective view of the distal end rigid member 10 when seen from an obliquely back side. Note that although FIGS. 1 to 3 illustrate some of members in a simplified manner for easiness of understanding of each member, FIG. 4 illustrates a more specific configuration example of the distal end rigid member 10.

The distal end rigid member 10 with a columnar shape is provided inside the distal end portion 5. The distal end rigid member 10 includes an end portion 10a on the distal end side in the direction of the longitudinal axis LX (hereinafter, referred to as a distal end-side end portion) and an end portion 10b on the proximal end side in the direction of the longitudinal axis LX (hereinafter, referred to as a proximal end-side end portion).

A plurality of holes 10c and 10d are formed in the distal end rigid member 10 in the direction of the longitudinal axis LX of the insertion portion 2. An image pickup unit 11 is disposed in and secured to one hole 10c in the distal end rigid member 10. The plurality of holes 10d are for a light guide for illumination, a channel for a treatment instrument, and the like.

As described above, the distal end rigid member 10 is disposed on the distal end side of the insertion portion 2 of the endoscope 1 in the direction of the longitudinal axis LX and configures a distal end rigid portion including the distal end-side end portion 10a and the proximal end-side end portion 10b in the direction of the longitudinal axis LX and the hole 10c provided in the direction of the longitudinal axis LX.

The bending portion 6 includes a plurality of bending pieces. A distal end bending pieces 6a of the bending portion 6 has a tubular shape, for example, a cylindrical shape. As illustrated by dashed lines in FIG. 2, the distal end bending pieces 6a are fitted to cover an outer peripheral portion of the distal end rigid member 10 on the proximal end side and are secured to the distal end rigid member 10 with screws, an adhesive, or the like.

As illustrated in FIG. 2, the image pickup unit 11 includes an objective optical unit 12 and a camera unit 13. The objective optical unit 12 includes a plurality of lenses, a cover glass, and the like as illustrated by dashed lines. The camera unit 13 includes a prism unit 21 and an image pickup device 22 as illustrated by one-dotted chain lines.

The objective optical unit 12 is thus a first optical system inserted and attached to the inside of the hole 10c in the distal end rigid member 10 in the direction of the longitudinal axis LX.

Figure 5:
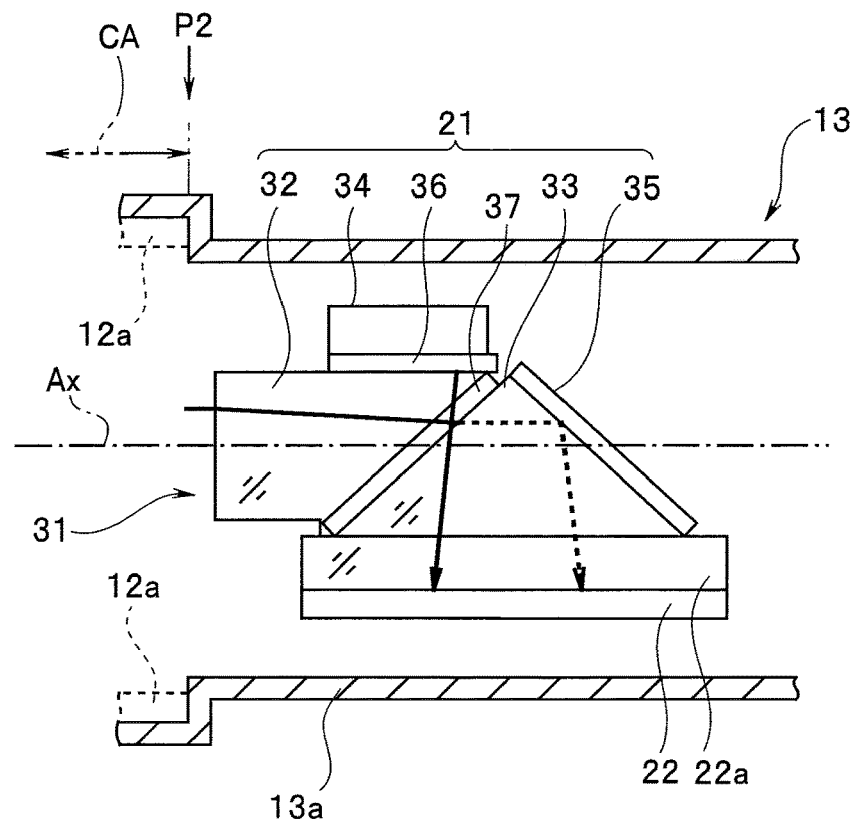
FIG. 5 is a diagram illustrating disposition of a prism unit and an image pickup device according to the embodiment of the present invention.

As described above, the objective optical unit 12 that is the first optical system includes lenses aligned and disposed inside a cylindrical member 12a (FIG. 5). The camera unit 13 that is a second optical system includes a prism that is an optical component that is heavier than the lenses of the objective optical unit 12 and the image pickup device 22, which are provided inside a cylindrical member 13a (FIG. 5) connected to the cylindrical member 12a.

A distal end-side portion of the cylindrical member 13a of the camera unit 13 is fitted to cover a proximal end-side portion of the cylindrical member 12a of the objective optical unit 12 (see FIG. 5). An adhesive is applied to the outer peripheral portion of the proximal end portion of the objective optical unit 12, and a distal end tubular portion of the camera unit 13 is fixed to the proximal end-side portion of the objective optical unit 12. A portion at which the distal end-side portion of the camera unit 13 and the proximal end-side portion of the objective optical unit 12 are fitted is a fitting adhesion portion CA that serves as a connecting portion.

In other words, the fitting adhesion portion CA that is the connecting portion between the objective optical unit 12 and the camera unit 13 is a portion that secures the objective optical unit 12 and the camera unit 13 by an inner peripheral portion of one of the objective optical unit 12 and the camera unit 13 being fitted such that the inner peripheral portion covers an outer peripheral portion of the other one of the objective optical unit 12 and the camera unit 13.

The image pickup unit 11 is inserted into the hole 10c (see FIG. 4) in the distal end rigid member 10 and is secured to the hole 10c with an adhesive or the like.

In the present embodiment, the prism unit 21 of the image pickup unit 11 includes two prisms to widen a depth of field. Since each of the two prisms has a three-dimensional shape made of a mass of a transparent optical material, the camera unit 13 according to the present embodiment has a larger mass than the camera unit 13 configured mainly of the image pickup device 22 as in the related art.

FIG. 5 is a diagram illustrating disposition of the prism unit 21 and the image pickup device 22.

As described above, the distal end-side portion of the cylindrical member 13a of the camera unit 13 is fitted to the proximal end-side portion of the cylindrical member 12a of the objective optical unit 12. Light from the subject is transmitted through the cover glass, which is not illustrated, from the objective optical unit 12 and is then incident on the prism unit 21 along an optical axis Ax of the objective optical unit 12.

As illustrated in FIG. 5, the prism unit 21 includes a polarization beam splitter 31. The prism unit 21 includes two prisms 32 and 33 that configure the polarization beam splitter 31, mirrors 34 and 35, and a λ/4 plate 36 that is a ¼ wavelength plate.

The polarization beam splitter 31 splits a subject image into two optical images with different focuses. The prism 32 is a prism on the subject side while the prism 33 is a prism on the image side.

Both the prisms 32 and 33 include beam split surfaces with an inclination of 45 degrees with respect to the optical axis Ax.

A polarization separation film 37 is formed on the beam split surface of the prism 32. The two prisms 32 and 33 configure the polarization beam splitter 31 by causing the beam split surfaces to abut each other via the polarization separation film 37.

The mirror 34 is provided in the vicinity of an end surface of the prism 32 via the λ/4 plate 36.

The image pickup device 22 is disposed at an end surface of the prism 33 via a cover glass 22a.

Light of the subject image from the objective optical unit 12 is separated into a P polarized component and an S polarized component by the polarization separation film 37 of the prism 32. The P polarized component is transmitted light while the S polarized component is reflected light. In other words, the subject image from the objective optical unit 12 is separated into two optical images, namely an optical image of the reflected light and an optical image of the transmitted light.

The optical image of the S polarized component is reflected on a side facing the image pickup device 22 by the polarization separation film 37, is transmitted through the λ/4 plate 36, is then reflected by the mirror 34, and is turned back to the image pickup device 22 side, as illustrated by a solid line. The optical image turned back is transmitted through the λ/4 plate 36 again, the polarization direction is thus rotated by 90 degrees, and the optical image is transmitted through the polarization separation film 37 and is formed on the image pickup surface of the image pickup device 22.

The optical image of the P polarized component is transmitted through the polarization separation film 37, is reflected by the mirror 35 provided on the opposite side of the beam split surface of the prism 33 toward the image pickup device 22, and is formed on the image pickup surface of the image pickup device 22 as illustrated by dashed lines.

A prism path is set such that a predetermined optical path difference of about several tens of μm, for example, is generated between an optical path for S polarization and an optical path for P polarization, and two optical images with different focuses are caused to be formed on a light receiving surface of the image pickup device 22.

In other words, the prisms 32 and 33 are disposed such that the optical path length on the reflected light side is shorter than the optical path length (path length) on the transmitted light side reaching the image pickup device 22 through the prism 33 in order to enable the subject image to be split into two optical images with different focusing positions.

As described above, the camera unit 13 is the second optical system connected to the proximal end side of the objective optical unit 12 in the direction of the longitudinal axis LX via the fitting adhesion portion CA that is the connecting portion and provided on the proximal end side in the direction of the longitudinal axis LX relative to the proximal end-side end portion 10b of the distal end rigid member 10.

The two prisms 32 and 33 takes an optical image of the subject on the distal end side of the distal end rigid member 10 in the direction of the longitudinal axis LX via the objective optical unit 12, convert the optical image into a first optical image focused on a near point and a second optical image focused on a far point, and cause each of the first optical image and the second optical image to be formed on the image pickup surface of the image pickup device 22.

Thus, the endoscope 1 can obtain an image with a wide depth of field by acquiring the optical images with two different focuses and generating a synthesized image with the aforementioned configuration.

Next, a configuration of a projecting portion of the distal end rigid member 10 will be described. The distal end rigid member 10 includes a projecting portion 14 projecting on the proximal end side as illustrated in FIGS. 2, 3, and 4.

The projecting portion 14 projects on the proximal end side from the proximal end-side end portion 10b of the distal end rigid member 10 when the distal end portion 5 is seen from the side surface and projects up to a position exceeding the proximal end portion of the prism unit 21, as illustrated in FIG. 2. The projecting portion 14 projects on the proximal end side along an outer peripheral surface of the distal end rigid member 10 with a columnar shape. As illustrated in FIG. 3, the sectional shape of the projecting portion 14 that perpendicularly intersects the longitudinal axis LX of the insertion portion 2 has a partially circular shape that partially includes a missing portion in one example.

The projecting portion 14 is formed on the proximal end side of the distal end rigid member 10 so as to cover a part of a side surface of the camera unit 13 in a range of an angle θ around an axis of the image pickup unit 11 as illustrated in FIG. 3. The angle θ is an angle that is equal to or greater than 180 degrees that is a size that makes it difficult for the camera unit 13 to drop off from the projecting portion 14, for example.

In other words, the projecting portion 14 is formed so as to cover at least a part of the periphery of the fitting adhesion portion CA that is the connecting portion. The projecting portion 14 is formed to cover the periphery of the fitting adhesion portion CA in a range that is greater than 180 degrees around an axis of the camera unit 13.

Each of two end surfaces 14e1 and 14e2 of the projecting portion 14 in a circumferential direction of the camera unit 13 is a plane, and the two end surfaces 14e1 and 14e2 are formed to be located in the same plane.

The two end surfaces 14e1 and 14e2 perpendicularly intersect a plane passing through a center axis C0 of the distal end rigid member 10 and a center axis C1 of the hole 10c.

The fitting adhesion portion CA is a portion at which the cylindrical portion of the camera unit 13 on the distal end side and the cylindrical portion of the objective optical unit 12 on the proximal end side are fitted in the direction of the longitudinal axis LX as described above. When the position of the distal end surface of the cylindrical member 13a of the camera unit 13 in the direction of the longitudinal axis LX is defined as P1, and the position of the proximal end surface of the cylindrical member 12a of the objective optical unit 12 in the direction of the longitudinal axis LX is defined as P2 in FIG. 2, the fitting adhesion portion CA is a portion within a range between the position P1 and the position P2 of the image pickup unit 11 in the direction of the longitudinal axis LX.

The projecting portion 14 projects from a position P0 of the proximal end-side end portion 10b of the distal end rigid member 10 to a position P3 in the direction of the longitudinal axis LX of the distal end rigid member 10. The position P3 is a position exceeding a gravity center position BP of the camera unit 13 from the position P0 of the proximal end-side end portion 10b of the distal end rigid member 10.

In other words, the projecting portion 14 projects by the length that is equal to or greater than the length from the proximal end-side end portion 10b of the distal end rigid member 10 to the gravity center position BP of the camera unit 13 in the direction of the longitudinal axis LX.

Here, the projecting portion 14 of the distal end rigid member 10 is formed to project by a length LE in the direction on the proximal end side from the proximal end-side end portion 10b as illustrated in FIG. 2.

Effects

Next, effects of the aforementioned endoscope will be described.

As described above, the distal end rigid member 10 includes the projecting portion 14 on the proximal end side of the distal end rigid member 10. The projecting portion 14 projects in the direction on the proximal end side from the proximal end-side end portion 10b at an angle θ that is equal to or greater than 180 degrees around the center axis C1 of the hole 10c only at a part of the periphery of the hole 10c in the distal end rigid member 10.

Since this makes it difficult for an interference with other components to occur even if optical devices such as prisms are provided in the camera unit 13, it is not necessary to increase the distal end rigid member 10 in size to secure a relief dimension with respect to other components, the length of the distal end rigid portion does not increase, and small-turning performance of the distal end portion 5 is thus not degraded.

Further, it is possible to prevent a failure from occurring at the fitting adhesion portion CA between the objective optical unit 12 and the camera unit 13 regardless of a direction in which an impact is applied to the distal end portion 5 and the camera unit 13 is swung over the entire periphery of 360 degrees of the distal end portion 5.

A proximal end surface 14a of the projecting portion 14 is located at the position P3 in the direction of the longitudinal axis LX. The position P3 is a position exceeding the gravity center position BP of the camera unit 13 from the position P0 of the proximal end-side end portion 10b of the distal end rigid member 10.

In this manner, the camera unit 13 is fixedly supported by the projecting portion 14, and it is possible to prevent the center of gravity of the camera unit 13 from being swung, even if an impact is applied to the distal end portion 5.

Note that it is only necessary for the proximal end surface 14a of the projecting portion 14 to be located at least at the position P2 on the proximal end side relative to the distal end rigid member 10. In other words, it is only necessary for the proximal end surface 14a of the projecting portion 14 to be located at least at the position P2 of the proximal end portion of the fitting adhesion portion CA on the proximal end side in the direction of the longitudinal axis LX such that the range from the proximal end-side end portion 10b to the proximal end portion of the fitting adhesion portion CA is covered with the projecting portion 14.

In that case, the projecting portion 14 of the distal end rigid member 10 projects in the direction of the proximal end by a length LE1 as illustrated in FIG. 2. Such a configuration can also prevent the fitting adhesion portion CA between the objective optical unit 12 and the camera unit 13 from breaking even if an impact is applied to the distal end portion 5 and the camera unit 13 is swung.

Further, the proximal end surface 14a of the projecting portion 14 may be located up to a position P4 of the proximal end portion 13b of the camera unit 13. In that case, the projecting portion 14 of the distal end rigid member 10 projects in the direction of the proximal end by a length LE2 as illustrated in FIG. 2.

In other words, the projecting portion 14 may project by the length that is equal to or greater than the length from the proximal end-side end portion 10b of the distal end rigid member 10 to the proximal end portion 13b of the camera unit 13 in the direction of the longitudinal axis LX.

Such a configuration can also prevent a failure from occurring at the fitting adhesion portion CA between the objective optical unit 12 and the camera unit 13 even if an impact is applied to the distal end portion 5 and the camera unit 13 is swung.

As described above, the projecting portion 14 projects on the proximal end side in the direction of the longitudinal axis LX by the length that is equal to or greater than the length from the proximal end-side end portion 10b of the distal end rigid member 10 to the position P2 of the proximal end portion of the fitting adhesion portion CA in the direction of the longitudinal axis LX at least at a part of the periphery of the hole 10c in the distal end rigid member 10.

Therefore, according to the aforementioned embodiment, it is possible to provide an endoscope capable of making it difficult for a failure to occur at the fitting adhesion portion between the objective optical unit and the camera unit even if a member with a large mass is disposed on the proximal end side of the distal end rigid portion, without degrading small-turning performance of the distal end portion.

Extending the entire outer peripheral portion on the proximal end side of the distal end rigid member 10 up to the proximal end side of the image pickup unit to prevent a failure from occurring at the fitting adhesion portion CA is also conceivable. However, the length of an internal component projecting portion of the camera unit projecting on the proximal end side from the distal end rigid member cannot be shortened to maintain the strength to protect the internal components. Further, the length of the internal component projecting portion of the camera unit cannot be shortened to maintain operability of assembling the distal end portion during fabrication. This leads to a problem that the length of the distal end rigid portion further increases.

Also, if the entire outer peripheral portion on the proximal end side of the distal end rigid member is extended up to the proximal end side of the image pickup unit, there is a concern that the internal components of the camera unit and inner walls of the distal end bending pieces may cause contact or an interference and the internal components of the camera unit may be affected by an unexpected force when the bending portion is bent.

On the other hand, according to the aforementioned embodiment, it is possible to prevent a failure from occurring at the fitting adhesion portion CA while maintaining the strength to protect the internal components and the operability of assembling the distal end portion during fabrication since the projecting portion 14 is provided so as to cover only a part of the outer peripheral portion of the camera unit 13.

Further, it is also possible to avoid contact or an interference between the internal components of the camera unit 13 and the inner walls of the distal end bending pieces 6a when the bending portion 6 of the insertion portion 2 is bent and to avoid a pressing force imparted to the internal components when the bending portion is bent.

Next, modifications of the aforementioned embodiment will be described.

Note that since an endoscope according to each of the following modifications has substantially the same configuration as the configuration of the endoscope according to the aforementioned embodiment, description of the same components as the components of the endoscope according to the aforementioned embodiment will be omitted, and only different configurations will be described.

First Modification

Although the two end surfaces of the projecting portion 14 in the circumferential direction are in the same plane in the aforementioned embodiment, two end surfaces of the projecting portion 14 in the circumferential direction are not in the same plane though the two end surfaces are parallel to each other in a first modification.

Figure 6:
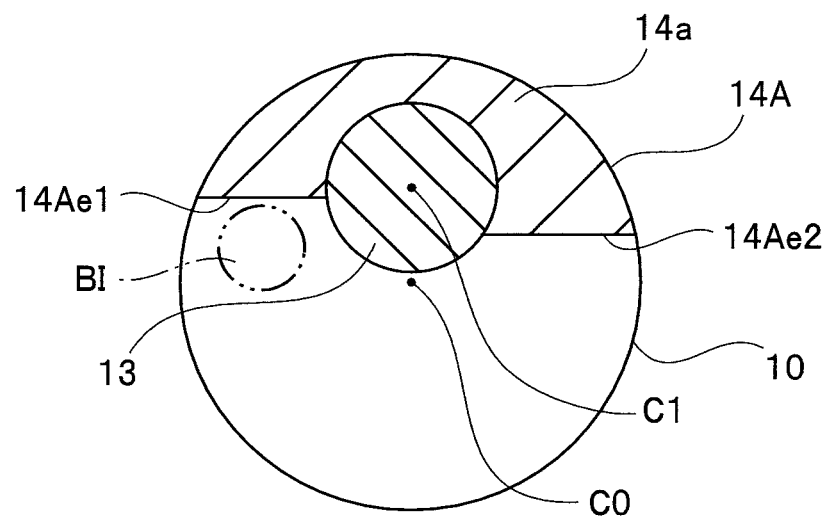
FIG. 6 is a sectional view of a distal end rigid member and an image pickup unit along the line III-III in FIG. 2, according to a first modification of the embodiment of the present invention.

FIG. 6 is a sectional view of a distal end rigid member 10 and the image pickup unit along the line III-III in FIG. 2 according to the first modification.

As illustrated in FIG. 6, a projecting portion 14A is formed such that two end surfaces 14Ae1 and 14Ae2 of the projecting portion 14A in the circumferential direction are not in the same plane.

Even in the first modification, the projecting portion 14A is formed on the proximal end side of the distal end rigid member 10 so as to surround a range of an angle of equal to or greater than 180 degrees, for example, similarly to the aforementioned embodiment, around the axis of the image pickup unit 11 as illustrated in FIG. 6.

Note that the two end surfaces 14Ae1 and 14Ae2 perpendicularly intersect the plane passing through the center axis C0 of the distal end rigid member 10 and the center axis C1 of the camera unit 13 in this case as well.

In the first modification, the end surface 14Ae1 is further separated from the center axis C0 of the distal end rigid member 10 than the end surface 14Ae2, and another internal component BI can thus be disposed in the vicinity of the end surface 14Ae1 as illustrated by two-dotted chain lines in FIG. 6.

Thus, the first modification has an effect that a space where another internal component BI is disposed can be widened as compared with the aforementioned embodiment, in addition to the effects of the aforementioned embodiment.

Second Modification

Although the projecting portion 14 is formed on the proximal end side of the distal end rigid member 10 so as to surround the range of the predetermined angle θ around the axis of the image pickup unit 11 in the aforementioned embodiment, a projecting portion 14B is provided on the proximal end side of the distal end rigid member 10 so as to surround a range of 360 degrees around the axis of the image pickup unit 11 in a second modification.

Figure 7:
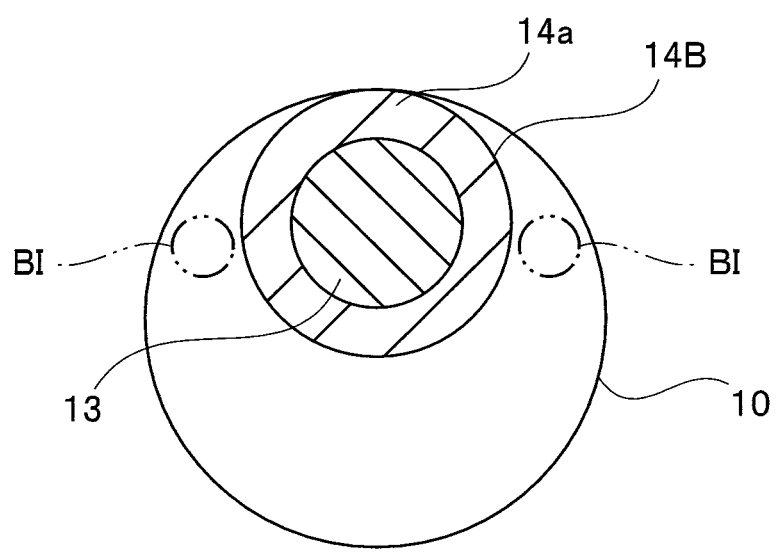
FIG. 7 is a sectional view of a distal end rigid member and an image pickup unit along the line III-III in FIG. 2, according to a second modification of the embodiment of the present invention.

FIG. 7 is a sectional view of the distal end rigid member 10 and the image pickup unit along the line III-III in FIG. 2 according to the second modification.

As illustrated in FIG. 7, the projecting portion 14B is formed on the proximal end side of the distal end rigid member 10 so as to surround the range of 360 degrees around the axis of the image pickup unit 11.

According to the second modification, the projecting portion 14B is formed to cover only the periphery of the camera unit 13 as illustrated in FIG. 7, and another internal component BI can thus be disposed in the vicinity of the projecting portion 14B as illustrated by two-dotted chain line in FIG. 7.

Thus, the second modification has an effect that a space where another internal component BI is disposed can be widened as compared with the aforementioned embodiment, in addition to the effects of the aforementioned embodiment.

Third Modification

Although the projecting portion 14B is formed on the proximal end side of the distal end rigid member 10 so as to surround the range of 360 degrees around the axis of the image pickup unit 11 in the aforementioned second modification, a projecting portion 14C is provided on the proximal end side of the distal end rigid member 10 so as to surround a range of equal to or greater than 180 degrees and less than 360 degrees around the axis of the image pickup unit 11 in a third modification.

Figure 8:
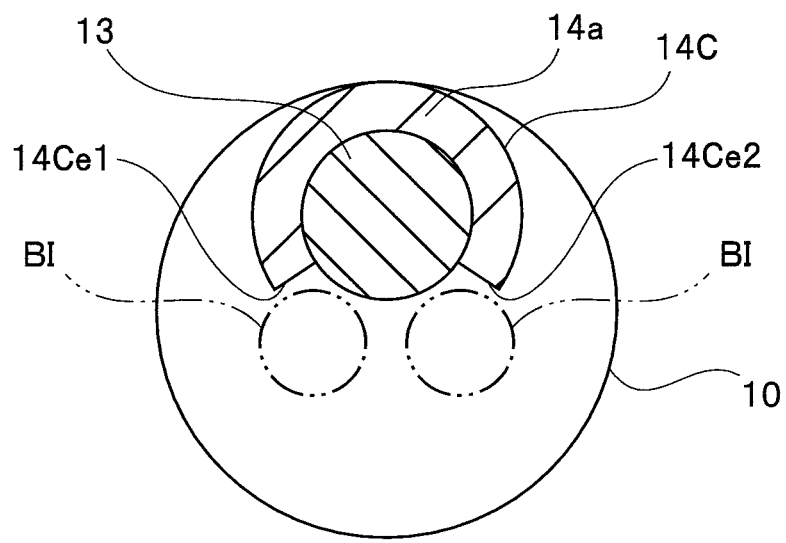
FIG. 8 is a sectional view of a distal end rigid member and an image pickup unit along the line III-III in FIG. 2, according to a third modification of the embodiment of the present invention.

FIG. 8 is a sectional view of the distal end rigid member 10 and the image pickup unit along the line III-III in FIG. 2 according to the third modification.

As illustrated in FIG. 8, the projecting portion 14C is formed on the proximal end side of the distal end rigid member 10 so as to surround the range of equal to or greater than 180 degrees and less than 360 degrees around the axis of the image pickup unit 11.

According to the third modification, the projecting portion 14C is formed at least at a part of the periphery of the camera unit 13 as illustrated in FIG. 8. As illustrated in FIG. 8, a portion of the internal component BI is disposed in the periphery of the hole 10c.

Thus, the third modification has an effect that a space where another internal component BI is disposed can be widened as compared with the aforementioned second modification as illustrated by two-dotted chain line in FIG. 8, in addition to the effects of the aforementioned embodiment.

Note that each of two end surfaces 14Ce1 and 14Ce2 of the projecting portion 14C in the circumferential direction may be on the same plane.

Figure 9:
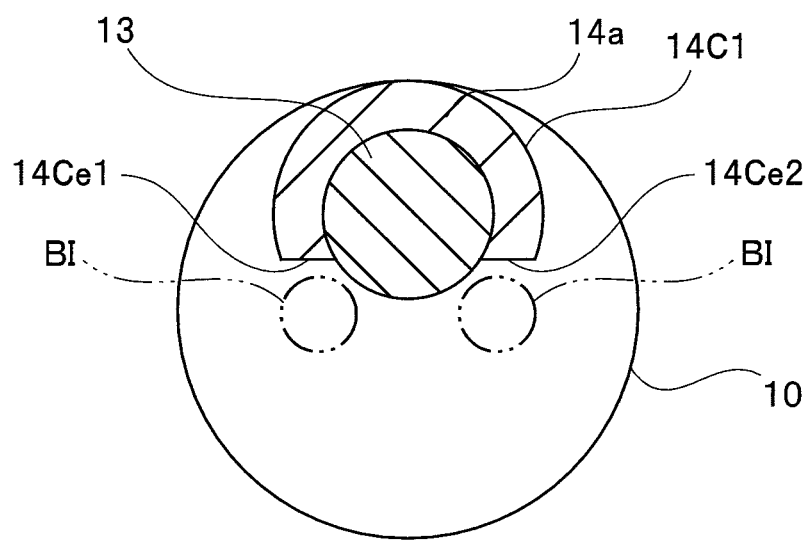
FIG. 9 is a sectional view of a distal end rigid member and an image pickup unit along the line III-III in FIG. 2, according to another example of the third modification of the embodiment of the present invention.

FIG. 9 is a sectional view of the distal end rigid member 10 and the image pickup unit along the line III-III in FIG. 2 according to another example of the third modification.

Although the two end surfaces 14Ce1 and 14Ce2 of the projecting portion 14C in the circumferential direction are not in the same plane in FIG. 8, two end surfaces 14Ce1 and 14Ce2 of a projecting portion 14C1 in the circumferential direction are formed to be in the same plane similarly to the aforementioned embodiment in FIG. 9.

The projecting portion 14C1 illustrated in FIG. 9 has an effect that workability during fabrication of the projecting portion 14C1 is improved, in addition to the effects that the projecting portion 14C illustrated in FIG. 8 has.

Fourth Modification

Although the proximal end surface 14a of the projecting portion projecting from the proximal end-side end portion 10b of the distal end rigid member 10 is in one plane that is parallel to the proximal end surface 14a in each of the aforementioned embodiment and the modifications, the proximal end surface 14a of the projecting portion is formed to have a step difference portion in the fourth modification.

Figure 10:
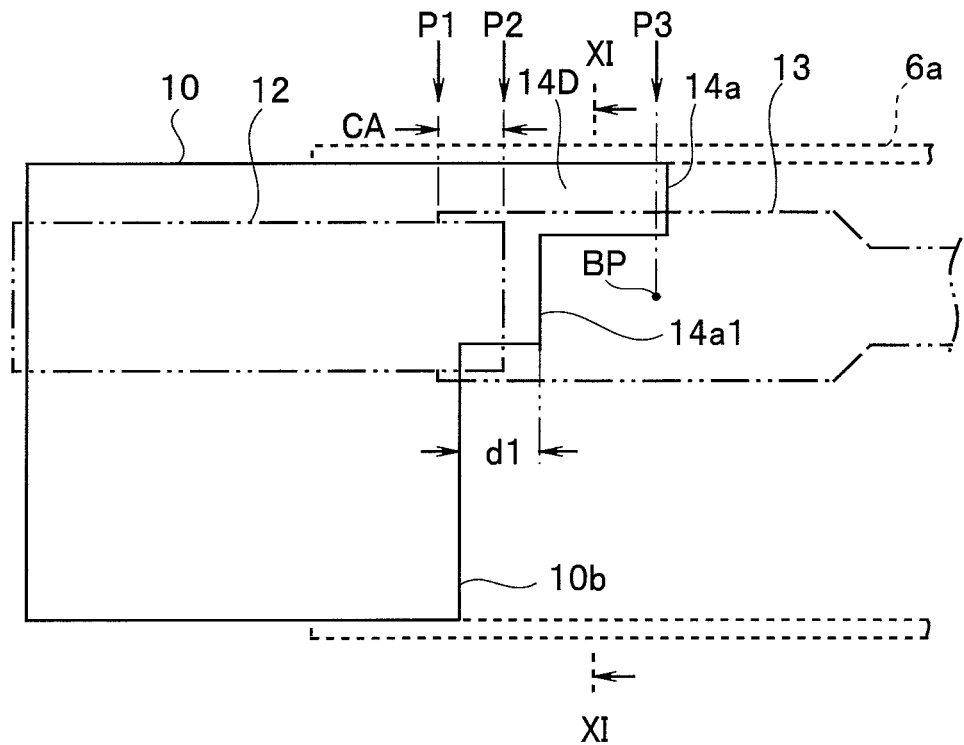
FIG. 10 is a side view of a distal end rigid member along the line III-III in FIG. 2, according to a fourth modification of the embodiment of the present invention.
Figure 11:
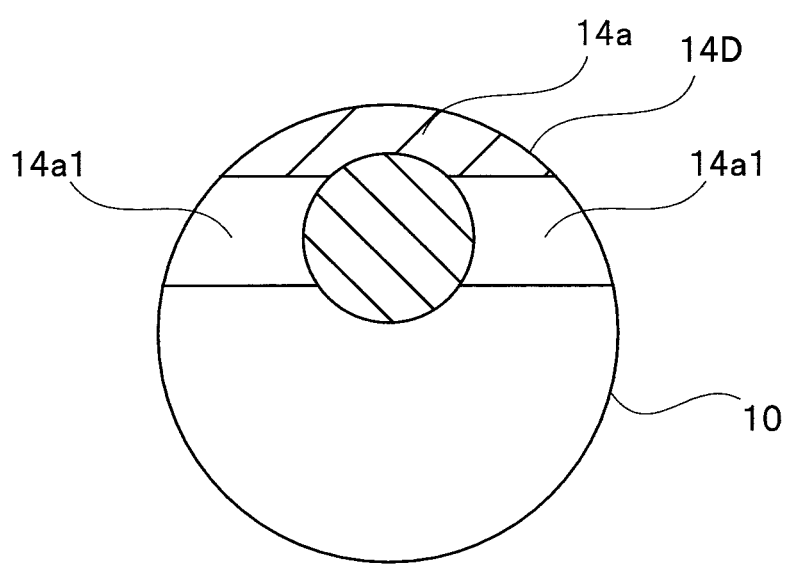
FIG. 11 is a sectional view of the distal end rigid member along a line XI-XI in FIG. 10.

FIG. 10 is a side view of the distal end rigid member 10 along the line III-III in FIG. 2 according to the fourth modification. FIG. 11 is a sectional view of the distal end rigid member 10 along a line XI-XI in FIG. 10.

As illustrated in FIG. 10, a projecting portion 14D has a step difference portion 14a1 at a location separated from the proximal end-side end portion 10b of the distal end rigid member 10 by a distance d1. The distance d1 from the proximal end-side end portion 10b to the step difference portion 14a1 is a distance that is equal to or greater than the distance from the proximal end-side end portion 10b to at least the proximal end portion of the fitting adhesion portion CA. In FIG. 10, the proximal end portion of the fitting adhesion portion CA is indicated by the position P2.

It is possible to reduce a region where the projecting portion 14D interferes with another internal component BI, with the step difference portion 14a1. In a case of an internal component such as a pipe-shaped member covered with a flexible tube and including a portion, a part of which has an increased diameter, it is possible to dispose the portion with the increased diameter of the internal component in proximity to the projecting portion 14D with the portion with the increased diameter kept away from the projecting portion 14D.

Note that the projecting portion 14D may have an inclined surface portion instead of the step difference portion 14a1.

Figure 12:
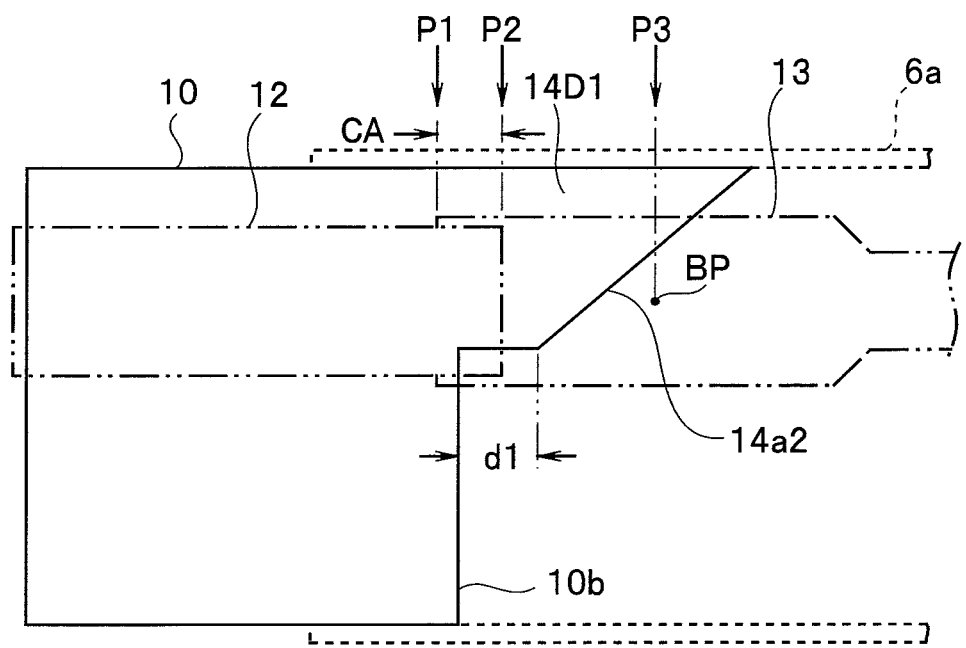
FIG. 12 is a side view of a distal end rigid member along the line III-III in FIG. 2, according to another example of the fourth modification of the embodiment of the present invention.

FIG. 12 is a side view of the distal end rigid member 10 along the line III-III in FIG. 2 according to another example of the fourth modification.

Although the step difference portion 14a1 is formed in the projecting portion 14D in FIG. 10, an inclined surface portion 14a2 is formed in a projecting portion 14D1 in FIG. 12. The inclined surface portion 14a2 is formed from a position at the aforementioned distance d1 from the proximal end-side end portion 10b.

The inclined surface portion 14a2 is inclined relative to the center axis C0 so as to be separated from the center axis C0 of the distal end rigid member 10 toward the proximal end side in the direction of the longitudinal axis LX.

The projecting portion 14D1 illustrated in FIG. 12 has effects similar to the effects of the projecting portion 14D illustrated in FIG. 10, and the proximal end portion of the projecting portion 14D1 is likely to warp since the projecting portion 14D1 is tapered toward the proximal end side in the direction of the longitudinal axis LX.

In the case of the projecting portion 14D illustrated in FIG. 10, there is a probability that when an impact is applied to the distal end portion 5, the projecting portion 14D is affected by an unexpected force in the vicinity of the proximal end-side end portion 10b of the distal end rigid member 10. On the other hand, in the case of the projecting portion 14D1 illustrated in FIG. 12, there is a probability that an unexpected force is imparted to the vicinity of the proximal end-side end portion 10b of the distal end rigid member 10 since the tapered portion of the projecting portion 14D1 warps when an impact is applied to the distal end portion 5.

Note that although the examples of the fourth modification illustrated in FIGS. 10 to 12 are examples applied to the projecting portion 14 according to the aforementioned embodiment, the fourth modification can also be applied to projecting portions with the shapes illustrated in the aforementioned first to third modifications.

Fifth Modification

Although the projecting portion in each of the aforementioned embodiment and the aforementioned modifications is a part of the distal end rigid member 10, is a part of the extending proximal end portion of the distal end rigid member 10, and is thus integral with the distal end rigid member 10, the projecting portion in this modification is a separate member from the distal end rigid member 10 and is provided to be secured to the proximal end-side end portion 10b of the distal end rigid member 10.

Figure 13:
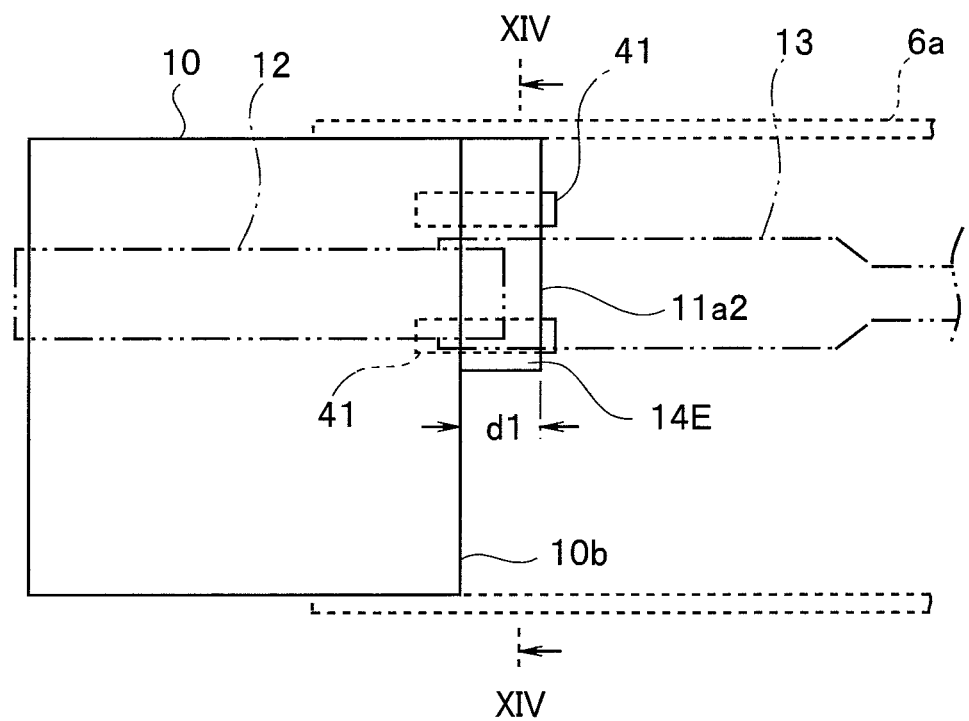
FIG. 13 is a side view of a distal end rigid member and a projecting portion along a center axis C0 of the distal end rigid member, according to a fifth modification of the embodiment of the present invention.

FIG. 13 is a side view of the distal end rigid member 10 and a projecting portion 14E along the center axis C0 of the distal end rigid member 10 according to a fifth modification.

Figure 14:
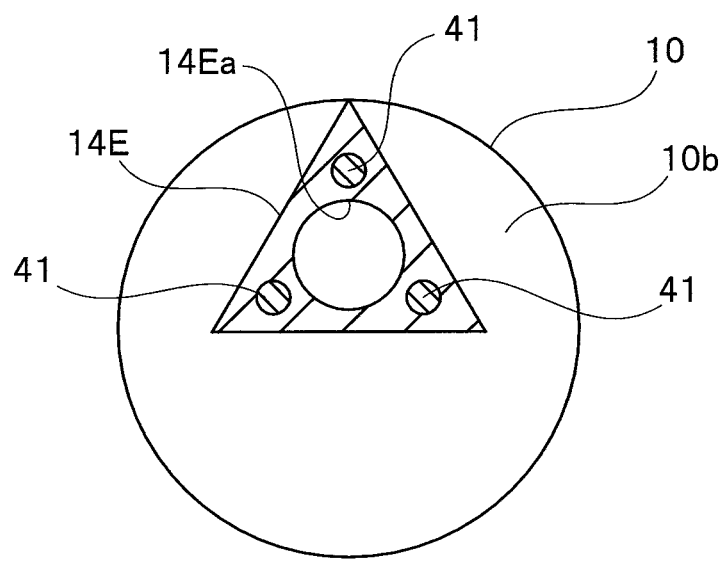
FIG. 14 is a sectional view of the projecting portion along a line XIV-XIV in FIG. 13.

FIG. 14 is a sectional view of the projecting portion 14E along a line XIV-XIV in FIG. 13.

As illustrated in FIG. 13, the projecting portion 14E has a triangular columnar shape or the like as an example and is secured to the proximal end-side end portion 10b of the distal end rigid member 10 with a plurality of screws 41.

A hole 10c into which the image pickup unit 11 is inserted is formed in the distal end rigid member 10, and a hole 14Ea with the same inner diameter as the inner diameter of the hole 10c is formed in the triangular columnar projecting portion 14E as well in the center axis direction of the triangular columnar shape. The image pickup unit 11 are inserted into and secured to these two holes 10c and 14Ea.

The projecting portion 14E has a plurality of, or three in this case, holes formed to be disposed at equal intervals around the hole 14Ea into which the image pickup unit 11 is inserted. The projecting portion 14E is secured to the proximal end-side end portion 10b of the distal end rigid member 10 by three screws 41 screwed into these three holes.

The fifth modification has an effect that the projecting portion 14E can have a complicated shape in accordance with the shape or the disposition of another internal component since the projecting portion 14E can be produced as a separate member, in addition to the effects of the aforementioned embodiment.

Note that although the projecting portion 14E is a separate member with the triangular columnar shape in the fifth modification illustrated in FIGS. 13 and 14, the fifth modification can also be applied to the aforementioned embodiment and the first to fourth modifications, and each of the projecting portions illustrated in the present embodiment and the first to fourth modifications may be a separate member.

Sixth Modification

Although the projecting portion is provided at the proximal end portion of the distal end rigid member 10 so as to surround a range of equal to or greater than 180 degrees around the axis of the image pickup unit 11 in each of the aforementioned embodiment and the modifications, the projecting portion in a sixth modification is formed to surround a range of less than 180 degrees around the axis of the image pickup unit 11.

Figure 15:
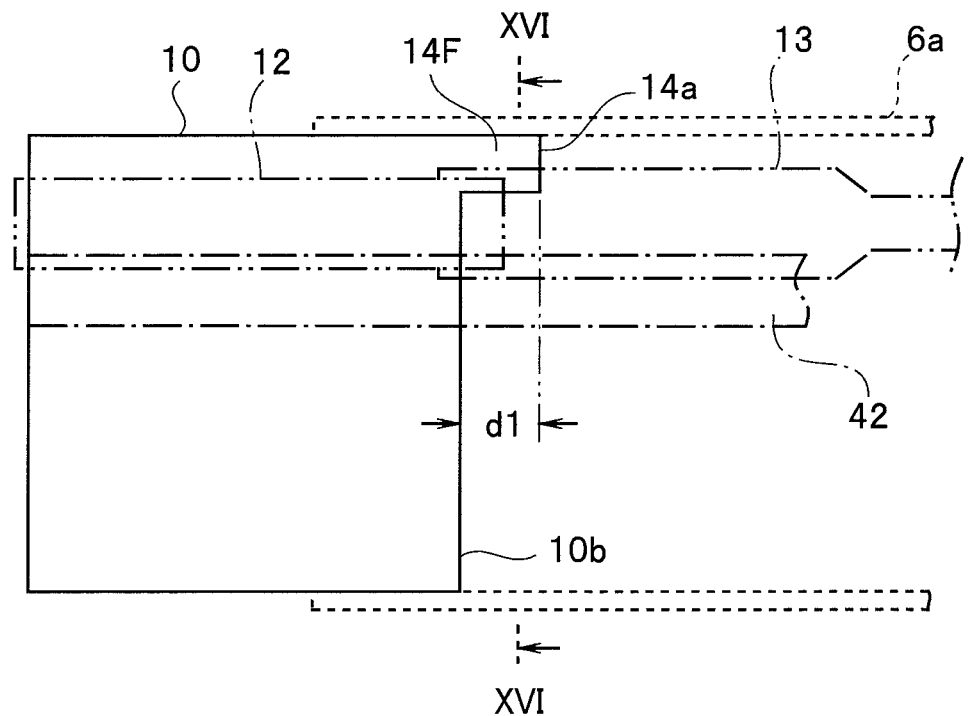
FIG. 15 is a side view of a distal end rigid member along a center axis C0 of the distal end rigid member, according to a sixth modification of the embodiment of the present invention.
Figure 16:
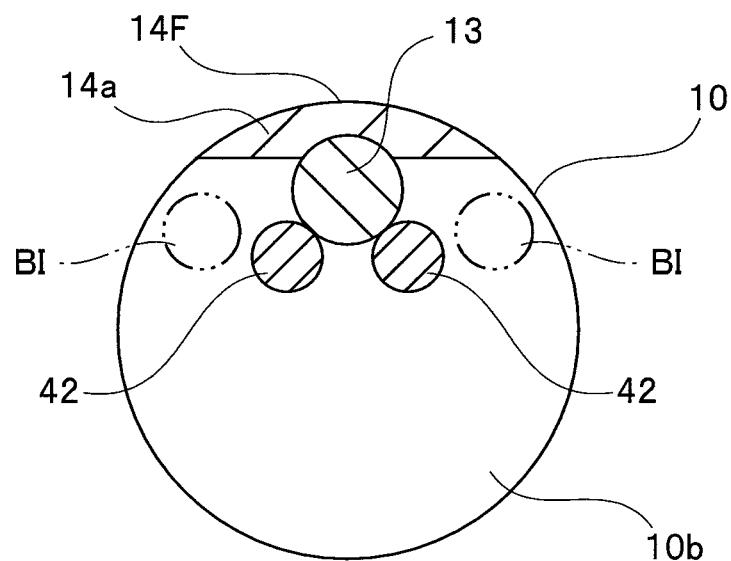
FIG. 16 is a sectional view of the distal end rigid member along a line XVI-XVI in FIG. 15.

FIG. 15 is a side view of the distal end rigid member 10 along the center axis C0 of the distal end rigid member 10 according to the sixth modification. FIG. 16 is a sectional view of the distal end rigid member 10 along a line XVI-XVI in FIG. 15.

The distal end rigid member 10 includes a projecting portion 14F projecting on the proximal end side. As illustrated in FIG. 16, although the projecting portion 14F surrounds only a range of less than 180 degrees around the axis of the image pickup unit 11, the image pickup unit 11 is supported with another internal component abutting on a side surface of the image pickup unit 11 on the opposite side of the projecting portion 14F.

In FIGS. 15 and 16, two light guides 42 are inserted into and secured to holes formed in the longitudinal axis direction of the distal end rigid member 10. As illustrated in FIG. 16, the light guides that are internal components are partially disposed in the periphery of the hole 10c.

The two light guides 42 are disposed such that side surfaces of the two light guides 42 abut the outer peripheral surface of the image pickup unit 11. Since a protection pipe is attached to each light guide 42, for example, two protection pipes of the two light guides 42 are caused to abut the outer peripheral surface of the image pickup unit 11.

Note that when the protection pipes are covered with protection tubes, the protection tubes with which the two protection pipes of the two light guides 42 are covered may abut the outer peripheral surface of the image pickup unit 11.

Further, although a member that supports the side surface of the image pickup unit 11 on the opposite side of the projecting portion 14F is the light guides 42, the member may be another internal component. For example, another internal component may be an air/water feeding pipe, a sub pipe for water feeding, an image pickup actuator unit, or the like.

Although the projecting portion 14F surrounds only the range of less than 180 degrees around the axis of the image pickup unit 11 as illustrated in FIG. 16, the side surface of the image pickup unit 11 on the opposite side of the projecting portion 14F is supported by two internal components, or in this case, the two light guides 42.

Thus, the sixth modification also has the effect that the space where another internal component BI is disposed can be widened as compared with the aforementioned embodiment as illustrated by two-dotted chain line in FIG. 16, in addition to the effects of the aforementioned embodiment.

Figure 17:
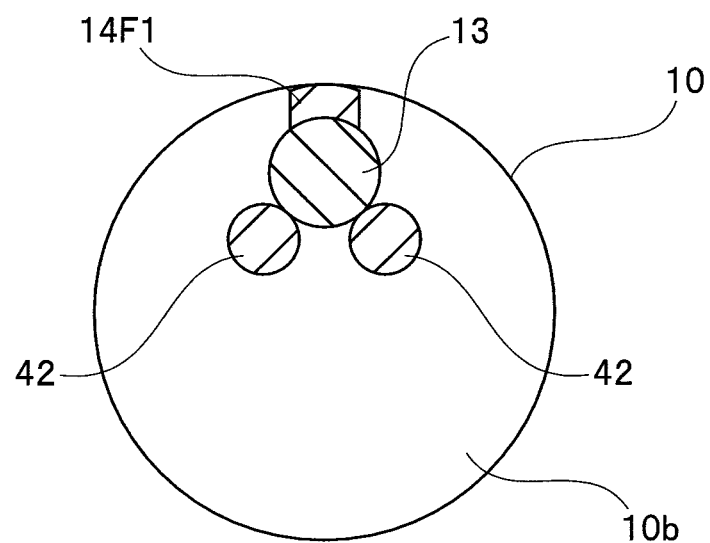
FIG. 17 is a sectional view of a distal end rigid member along the line XVI-XVI in FIG. 15, according to another example of the sixth modification of the embodiment of the present invention.

Note that although the projecting portion 14F in the sixth modification has a flat and partially circular section as illustrated in FIG. 16, the projecting portion 14F may have a rod shape as illustrated in FIG. 17. FIG. 17 is a sectional view of the distal end rigid member 10 along the line XVI-XVI in FIG. 15 according to another example of the sixth modification.

Although a surface of a projecting portion 14F1 on the camera unit 13 side in FIG. 17 has a curved surface along the outer peripheral surface of the image pickup unit 11, the projecting portion 14F1 has a rod shape as a whole.

The image pickup unit 11 is supported by the light guides 42 that serve as another internal component in FIG. 17 as well.

Thus, it is also possible to cause the projecting portion 14F1 in FIG. 17 to lead to effects equivalent to the effects of the projecting portion 14F illustrated in FIG. 16.

Note that although the projecting portion 14F1 in FIG. 17 is formed on the opposite side of the center axis C0 of the distal end rigid member 10, that is, on the outer peripheral side relative to the image pickup unit 11, the projecting portion may be formed on the same side as the center axis of the distal end rigid member 10, that is, on the center axis side relative to the image pickup unit 11.

Figure 18:
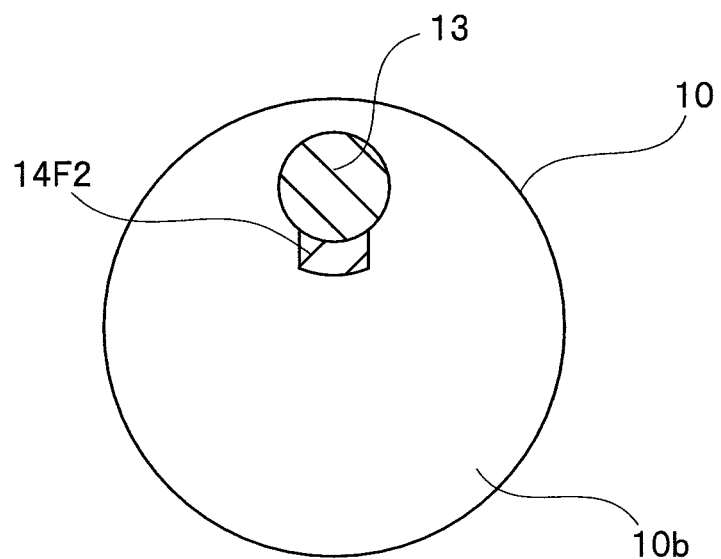
FIG. 18 is a sectional view of a distal end rigid member along the line XVI-XVI in FIG. 15, according to a yet another example of the sixth modification of the embodiment of the present invention.

FIG. 18 is a sectional view of the distal end rigid member 10 along the line XVI-XVI in FIG. 15 according to yet another example of the sixth modification.

Although a surface of a projecting portion 14F2 on the camera unit 13 side in FIG. 18 also has a curved surface along the outer peripheral surface of the image pickup unit 11, the projecting portion 14F2 has a rod shape as a whole.

The image pickup unit 11 is unlikely to be swung on the outer peripheral side of the distal end rigid member 10 due to the distal end bending pieces 6a. If the image pickup unit 11 attempts to swing due to an impact or the like applied to the distal end portion 5, the projecting portion 14F2 is provided on the center axis C0 side of the distal end rigid member 10, the side surface of the image pickup unit 11 on the center axis C0 side of the distal end rigid member 10 is supported by the projecting portion 14F2, and a failure is thus unlikely to occur at the fitting adhesion portion CA.

In the sixth modification, the projecting portions 14F and 14F1 may also be members separate from the distal end rigid member 10 as in the fifth modification.

As described above, according to each of the aforementioned embodiment and the modifications, it is possible to provide an endoscope capable of making it difficult for a failure to occur at the fitting adhesion portion between the objective optical unit and the camera unit even if a member with a large mass is disposed on the proximal end side of the distal end rigid portion, without degrading small-turning performance of the distal end portion.

Seventh Modification

Although the example in which the camera unit 13, at least a part of the periphery of which is covered with the projecting portion 14 of the distal end rigid member 10, is configured to include one image pickup device 22 with respect to the prism unit 21 has been described in each of the aforementioned embodiment and the modifications, the camera unit 13 is not limited to the aforementioned configuration, particularly, the configuration as in FIG. 5.

Figure 19:
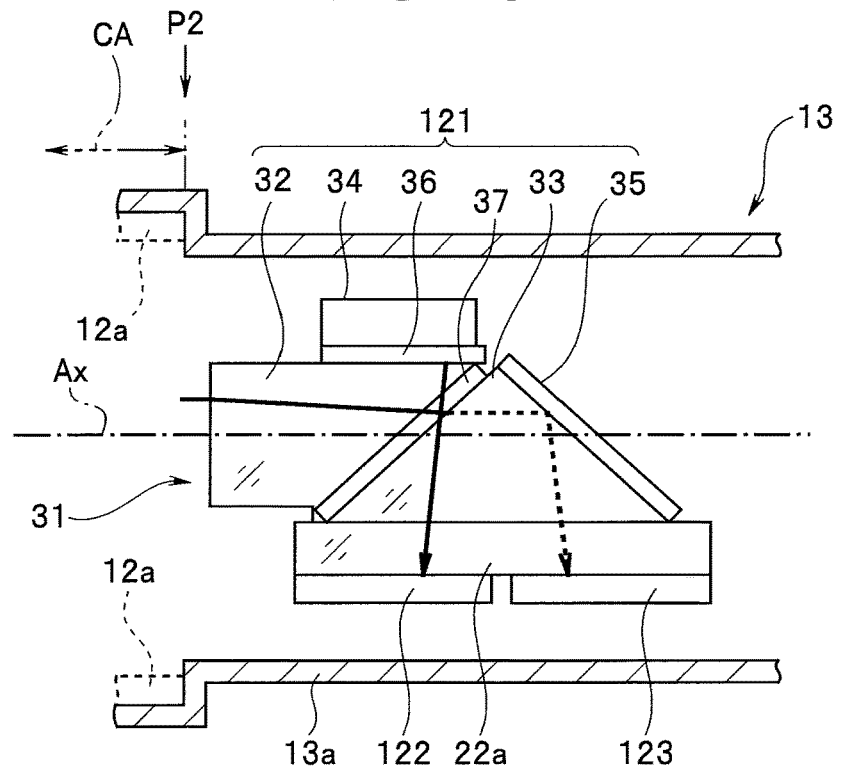
FIG. 19 is a diagram illustrating disposition of a prism unit and two image pickup devices according to a seventh modification of the embodiment of the present invention.

FIG. 19 is a diagram illustrating disposition of a prism unit 121 and image pickup devices 122 and 123.

As described above, the distal end-side portion of the cylindrical member 13a of the camera unit 13 is fitted to the proximal end-side portion of the cylindrical member 12a of the objective optical unit 12. Light from the subject is transmitted through the cover glass, which is not illustrated, from the objective optical unit 12 and is then incident on the prism unit 121 along the optical axis Ax of the objective optical unit 12.

As illustrated in FIG. 19, the prism unit 121 is different in that two image pickup devices (122 and 123) are provided although the prism unit 121 has functions similar to the functions illustrated in FIG. 5.

The optical image of the S polarized component is reflected by the polarization separation film 37 on the side facing the first image pickup device 122, is transmitted through the λ/4 plate 36, is reflected by the mirror 34, and is then turned back to the first image pickup device 122 side, as illustrated by the solid line. The optical image turned back is transmitted through the λ/4 plate 36 again, the polarization direction is thus rotated by 90 degrees, and the optical image is transmitted through the polarization separation film 37 and is formed on an image pickup surface of the first image pickup device 122.

The optical image of the P polarized component is transmitted through the polarization separation film 37, is reflected by the mirror 35 provided on the opposite side of the beam split surface of the prism 33 toward the second image pickup device 123, and is formed on an image pickup surface of the second image pickup device 123.

In this manner, the endoscope 1 can obtain an image with a wide depth of field by acquiring the optical images with two different focuses and generating a synthesized image with the aforementioned configuration, and it is possible to relatively reduce the size of the prism unit 121 since it is only necessary to dispose small-sized image pickup devices only at portions where the optical images are formed as compared with the afore-mentioned embodiment.

Eighth Modification

Figure 20:
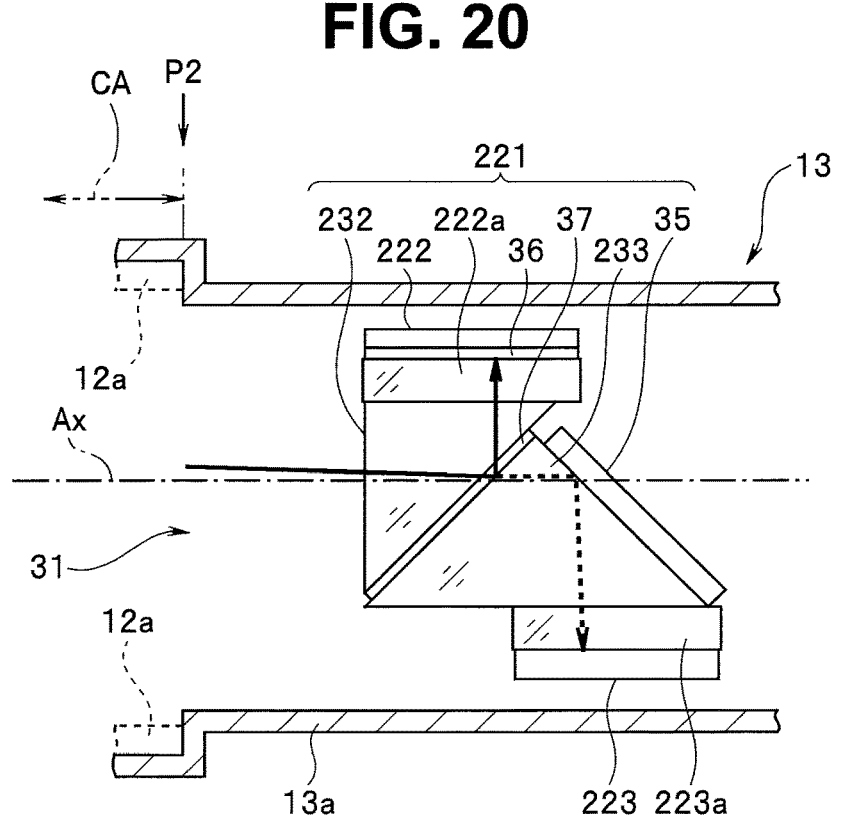
FIG. 20 is a diagram illustrating disposition of a prism unit and two image pickup devices according to an eighth modification of the embodiment of the present invention.

FIG. 20 is a diagram illustrating disposition of a prism unit 221 and image pickup devices 222 and 223. Although the present modification is similar to the aforementioned seventh modification, the prism shape differs from the prism shape in the seventh modification, and the present modification thus has a form in which the image pickup devices are not aligned.

The optical image of the S polarized component is reflected by the polarization separation film 37 on the image pickup device 222 side, passes through a cover glass 222a and the λ/4 plate 36, and is then formed on an image pickup surface of the image pickup device 222. The optical image of the P polarized component is transmitted through the polarization separation film 37, is reflected by the mirror 35 provided on the opposite side of a beam split surface of a prism 233 toward the image pickup device 223, passes through a cover glass 223a, and is then formed on an image pickup surface of the image pickup device 223.

The present modification thus has effects similar to the effects of the seventh modification.

Ninth Modification

Although the configuration in which the camera unit 13 acquires two optical images with different focuses with a predetermined optical path difference by causing the prism unit to form optical images at the same time on one or two image pickup devices and generates a synthesized image has been described in each aforementioned embodiment and modifications, a configuration in which no prism unit is included, two optical images with different focuses are acquired by causing the optical images to be formed with a time difference on the image pickup device, and a synthesized image is then generated may be employed.

FIG. 21 is a diagram illustrating a main configuration of a camera unit 313.

A distal end-side portion of a cylindrical member 13a of the camera unit 313 is fitted to the proximal end-side portion of the cylindrical member 12a of the objective optical unit 12. Light from the subject is transmitted from a cover glass, which is not illustrated, from the objective optical unit 12, is incident on a movable lens 332a of a movable lens unit 332 along the optical axis Ax of the objective optical unit 12, and forms an image as an optical image on an image pickup surface of an image pickup device 322 via a cover glass 322a.

The camera unit 313 includes a drive unit 501 that includes an actuator such as a motor and moves the movable lens 332a and is connected to a control unit 500 configured to control the drive unit 501 and the image pickup device 322.

The control unit 500 causes the movable lens 332a to perform an operation such as reciprocation by causing the drive unit 501 to drive and sets the movable lens 332a at different focus positions relative to the image pickup device 322.

The movable lens 332a has a setting of focusing at a first focus position and at a second focus position that is different from the first focus position relative to the image pickup device 322.

When the movable lens 332a reaches the first focus position relative to the image pickup device 322, the control unit 500 causes the image pickup device 322 to acquire a first image.

When the movable lens 332a reaches the second focus position relative to the image pickup device 322, the control unit 500 causes the image pickup device 322 to acquire a second image.

The thus obtained first image and second image are synthesized by a video processor which is connected to the endoscope 1 and is not illustrated in the drawing, and a depth enlarged image is outputted.

In the camera unit 313 with such a configuration, a component with a large mass is disposed on the proximal end side beyond the objective optical unit 12 similarly to the camera unit including prisms. Therefore, there is a concern that when an impact is applied to the distal end portion, a failure may occur at the fitting adhesion portion with the objective optical unit 12.

According to the aforementioned embodiment, since the projecting portion 14 is provided so as to cover a part of the outer peripheral portion of the camera unit 313, it is possible to prevent a failure from occurring at the fitting adhesion portion CA between the camera unit 313 and the proximal end-side portion of the objective optical unit 12 while maintaining the strength to protect the internal component and the operability of assembling the distal end portion during fabrication similarly to the camera unit including the prisms.

The present invention is not limited to the aforementioned embodiment, and various changes, modifications, and the like can be made without changing the gist of the present invention.

What is claimed is:

1. An endoscope comprising:
   a distal end body disposed on a distal end side of an insertion portion of the endoscope in a longitudinal axis direction, the distal end body including a distal end-side end portion and a proximal end-side end portion separated in the longitudinal axis direction and a hole extending in the longitudinal axis direction;
   a first optical system inserted into and attached to an inside of the hole; and
   a second optical system located proximally relative to the first optical system, the second optical system being connected to the first optical system at a connecting portion, the second optical system having a center of gravity positioned at a first distance from the proximal end-side end portion;
   wherein the distal end body comprises a projecting portion projecting proximally in the longitudinal axis direction from the proximal end-side end portion of the distal end body, the projection portion being disposed internally of the insertion portion, the projecting portion projecting a second distance from the proximal end-side portion, the second distance being equal to or greater than the first distance.

2. The endoscope according to claim 1, wherein the projecting portion overlaps at least a portion of the connecting portion in the longitudinal axis direction.

3. The endoscope according to claim 2, wherein the projecting portion is formed so as to cover a periphery of the second optical system in a range greater than 180 degrees around an axis.

4. The endoscope according to claim 1, wherein the projecting portion projects by a length that is equal to or greater than a length from the proximal end-side end portion of the distal end body to a proximal end portion of the second optical system in the longitudinal axis direction.

5. The endoscope according to claim 1, wherein the connecting portion between the first optical system and the second optical system is configured to secure the first optical system and the second optical system by an inner peripheral portion of one of the first optical system and the second optical system being fitted such that the inner peripheral portion covers an outer peripheral portion of an other one of the first optical system and the second optical system.

6. The endoscope according to claim 1, wherein the second optical system has a weight heavier than a weight of the first optical system.

7. The endoscope according to claim 6, wherein the second optical system includes a prism.

8. The endoscope according to claim 7, wherein:
   the second optical system further comprises an image pickup sensor; and
   the prism takes, via the first optical system, an optical image of a subject on a distal end side of the distal end body in the longitudinal axis direction, converts the optical image into a first optical image focused on a near point and a second optical image focused on a far point, and causes each of the first optical image and the second optical image to be formed on an image pickup surface of the image pickup sensor.

9. The endoscope according to claim 1, further comprising an internal component extending in the longitudinal axis direction, the internal component being provided inside the insertion portion,
   wherein a portion of the internal component is disposed at a position peripheral to the hole.

10. An endoscope comprising:
    a distal end body disposed on a distal end side of an insertion portion of the endoscope in a longitudinal axis direction, the distal end body including a distal end-side end portion and a proximal end-side end portion separated in the longitudinal axis direction and a hole extending in the longitudinal axis direction;
    a first optical system inserted into and attached to an inside of the hole; and
    a second optical system located proximally relative to the first optical system, the second optical system being connected to the first optical system at a connecting portion the second optical system having a center of gravity positioned at a first distance from the proximal end-side end portion;
    wherein the distal end body comprises a projecting portion projecting proximally in the longitudinal axis direction from the proximal end-side end portion of the distal end body, the projecting portion overlapping at least a portion of the connecting portion the projection portion being disposed internal of the insertion portion in the longitudinal axis direction, the projecting portion having a surface at least partially enveloping a periphery of the second optical system in a cross section taken along a plane perpendicular to the longitudinal axis direction and the projecting portion projecting a second distance from the proximal end-side portion, the second distance being equal to or greater than the first distance.

11. The endoscope according to claim 10, wherein the surface is configured to continuously extend in the longitudinal axis direction from the hole.

12. The endoscope according to claim 10, wherein the surface envelops 180 degrees or more of the periphery of the second optical system.

13. The endoscope according to claim 10, wherein the second optical system has a weight heavier than a weight of the first optical system.

14. The endoscope according to claim 13, wherein the second optical system includes a prism.

15. The endoscope according to claim 14, wherein:
    the second optical system further comprises an image pickup sensor; and the prism takes, via the first optical system, an optical image of a subject on a distal end side of the distal end body in the longitudinal axis direction, converts the optical image into a first optical image focused on a near point and a second optical image focused on a far point, and causes each of the first optical image and the second optical image to be formed on an image pickup surface of the image pickup sensor.

16. A distal end assembly comprising:
a distal end body disposed on a distal end side of an insertion portion of an endoscope in a longitudinal axis direction, the distal end body including a distal end-side end portion and a proximal end-side end portion separated in the longitudinal axis direction and a hole extending in the longitudinal axis direction;
   a first optical system inserted into and attached to an inside of the hole; and
   a second optical system located proximally relative to the first optical system, the second optical system being connected to the first optical system at a connecting portion, the second optical system having a center of gravity positioned at a first distance from the proximal end-side portion;
wherein the distal end body comprises a projecting portion projecting proximally in the longitudinal axis direction from the proximal end-side end portion of the distal end body, the projection portion being disposed internally of the insertion portion, the projecting portion projecting a second distance from the proximal end-side portion, the second distance being equal to or greater than the first distance.

17. The distal end assembly according to claim 16, wherein the projecting portion has a surface at least partially enveloping a periphery of the second optical system in a cross section taken along a plane perpendicular to the longitudinal axis direction.

18. The distal end assembly according to claim 17, wherein the projecting portion overlaps at least a portion of the connecting portion in the longitudinal axis direction.

19. The distal end assembly according to claim 16, wherein the projecting portion has a surface enveloping 180 degrees or more of the periphery of the second optical system.

20. An endoscope comprising:
   the insertion portion; and
   the distal end assembly according to claim 16 disposed in the distal end side of the insertion portion.

* * * * *